US00PP18373P2

(12) United States Plant Patent
Merkens

(10) Patent No.: US PP18,373 P2
(45) Date of Patent: Jan. 1, 2008

(54) ***EURYOPS* PLANT NAMED 'STRAESUN'**

(50) Latin Name: *Euryops anthanasiae*
Varietal Denomination: Straesun

(75) Inventor: Alfons Merkens, Straelen (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/343,861

(22) Filed: Jan. 31, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV–ROM GTITM, Plant Variety Database, 2006/04, GTI Jouve Retrieval Software, Citation for *Euryops*'Straesun' one page.*

* cited by examiner

*Primary Examiner*—Kent Bell
*Assistant Examiner*—June Hwu
(74) *Attorney, Agent, or Firm*—C A Whealy

(57) ABSTRACT

A new and distinct cultivar of *Euryops* plant named 'Straesun', characterized by its upright, compact and rounded plant habit; rough-textured and dark green-colored foliage; large inflorescences; and daisy-type inflorescences with bright yellow-colored ray florets and darker yellow-colored disc florets.

1 Drawing Sheet

Botanical designation: *Euryops anthanasiae.*
Cultivar denomination: 'Straesun'.

BACKGROUND OF THE INVENTION

The present invention relates to a new and distinct cultivar of *Euryops* plant, botanically known as *Euryops anthanasiae* and hereinafter referred to by the cultivar name 'Straesun'.

The new *Euryops* is a naturally-occurring branch mutation of an unnamed selection of *Euryops anthanasiae,* not patented. The cultivar Straesun was discovered and selected by the Inventor from within a population of plants of the parent selection in Straelen, Germany on Apr. 11, 2002.

Asexual reproduction of the new *Euryops* by terminal cuttings in a controlled environment in Straelen, Germany since Apr. 11, 2002, has shown that the unique features of the *Euryops* are stable and reproduced true to type in successive generations.

SUMMARY OF THE INVENTION

The new *Euryops* has not been observed under all possible environmental conditions. The phenotype may vary somewhat with variations in environment such as temperature and light intensity without, however, any variance in genotype.

The following characteristics have been repeatedly observed and are determined to be basic characteristics of 'Straesun' and distinguish the new *Euryops* as a new and distinct cultivar:

1. Upright, compact and rounded plant habit.
2. Rough-textured and dark green-colored foliage.
3. Large inflorescences.
4. Daisy-type inflorescences with bright yellow-colored ray florets and darker yellow-colored disc florets.

Plants of the new *Euryops* differ from plants of the parent selection primarily in inflorescence size as plants of the parent selection have smaller inflorescences than plants of the new *Euryops.*

Plants of the new *Euryops* can be compared to plants of the *Euryops* cultivar Sonnenschein, not patented. In side-by-side comparisons conducted in Stuttgart, Germany, plants of the new *Euryops* differed primarily from plants of the cultivar Sonnenschein in inflorescence size as plants of the cultivar Sonnenschein had smaller inflorescences than plants of the new *Euryops.*

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Euryops.*

The photograph comprises a side perspective view of a typical flowering plant of 'Straesun' grown in a container.

DETAILED BOTANICAL DESCRIPTION

The aforementioned photograph, following observations and averaged measurements describe plants grown in Stuttgart, Germany, in a glass-covered greenhouse. During the production of the plants, day temperatures ranged from 18° C. to 22° C., night temperatures ranged from 15° C. to 18° C. and light levels ranged from 20 to 55 kilolux. Plants were grown in 10-cm containers and were pinched one time about eight to ten days after planting. Plants had been growing for about four months when the photograph and description were taken. Color references are made to The Royal Horticultural Society Colour Chart, 1995 Edition, except where general terms of ordinary dictionary significance are used.

Botanical classification: *Euryops anthanasiae* cultivar Straesun.

Parentage: Naturally-occurring branch mutation of an unnamed selection of *Euryops anthanasiae,* not patented.

Propagation:

*Type.*—Terminal vegetative cuttings.

*Time to initiate roots, summer.*—About 12 to 14 days at 25° C.

*Time to initiate roots, winter.*—About 14 to 16 days at 25° C.

*Time to produce a rooted cutting, summer.*—About three to four weeks at 25° C.

*Time to produce a rooted cutting, winter.*—About four weeks at 25° C.

*Root description.*—Fine, fibrous; light creamy white in color.

*Rooting habit.*—Dense.

Plant description:

*General appearance.*—Inverted triangle; upright, compact and rounded plant form with inflorescences held above and beyond the foliage; moderately vigorous.

*Plant height* (*soil level to top of foliar plane*).—About 30 cm to 35 cm.

*Plant height* (*soil level to top of inflorescence plane*).—About 35 cm to 50 cm.

*Plant width.*—About 20 cm to 30 cm.

*Lateral branch* (*peduncle*) *description.*—Length: About 5 cm to 10 cm. Diameter: About 5 mm. Internode length: About 1 cm to 2 cm. Aspect: Upwardly curving. Texture: Smooth, glabrous. Strength: Moderately strong. Color: 142B overlain with 59B.

*Foliage description.*—Arrangement: Alternate, simple; sessile. Length: About 5 cm to 8 cm. Width: About 2 cm to 3 cm. Shape: Palmately lobed. Apex: Rounded. Base: Attenuate. Margin: Lobed. Texture, upper and lower surfaces: Smooth, glabrous. Venation pattern: Pinnate. Color: Developing and fully expanded foliage, upper surface: 138A; venation, 138A. Developing and fully expanded foliage, lower surface: 138B; venation, 138A.

Inflorescence description:

*Appearance.*—Daisy-type inflorescences with ligulate ray florets. Disc and ray florets develop acropetally on a capitulum. Solitary inflorescences held upright and outwardly on axillary peduncles. Inflorescences positioned mostly perpendicular to the peduncles. Inflorescences not persistent.

*Flowering response.*—Under natural conditions, plant flower from April to September in Germany; flowering continuous during this period.

*Inflorescence longevity.*—Inflorescences last about one week on the plant.

*Quantity of inflorescences.*—Freely flowering, about two to three open inflorescences per lateral branch.

*Fragrance.*—Moderate.

*Inflorescence size.*—Diameter: About 6 cm. Depth (height): About 1 cm. Diameter of disc: About 1.5 cm.

*Inflorescence buds.*—Height: About 5 mm. Diameter: About 1 cm. Shape: Ovoid. Color: 144C.

*Ray florets.*—Quantity per inflorescence: About 16 to 18 arranged in a single whorl. Shape: Ligulate to lanceolate. Length: About 2 cm. Width: About 6 mm. Apex: Rounded. Base: Attenuate. Margin: Entire. Texture, upper and lower surfaces: Smooth, glabrous. Aspect: Initially upright; with development, eventually close to perpendicular to the peduncle. Color: When opening and fully opened, upper surface: 12A. When opening and fully opened, lower surface: 12A.

*Disc florets.*—Arrangement: Massed at the center of the inflorescence. Quantity per inflorescence: Numerous, about 100. Shape: Tubular, elongated; apex, five-pointed; base, fused. Length: About 8 mm. Diameter: About 1 mm. Color: Immature: 14A. Mature: 16A.

*Involucral bracts* (*phyllaries*).—Quantity per inflorescence: About twelve. Length: About 1 cm. Width: About 6 mm. Shape: Deltoid. Apex: Acute. Base: Elongated. Margin: Entire. Texture, upper and lower surfaces: Smooth, glabrous. Color, upper and lower surfaces: 144C.

*Reproductive organs.*—Androecium: Only on disc florets. Stamen quantity per floret: Five. Anther length: About 1 mm. Anther shape: Oblong. Pollen color: 11A. Filament: Less than 1 mm in length: white in color. Gynoecium: Present on ray and disc florets. Pistil quantity per floret: One. Pistil length: About 5 mm. Stigma shape: Two-parted. Stigma color: Close to 9A. Style color: Close to 6A. Seed/fruit: Seed and fruit production has not been observed.

Disease/pest resistance: Resistance to pathogens and pests common to *Euryops* has not been observed on plants grown under commercial conditions.

Temperature/weather tolerance: Plants of the new *Euryops* have been observed to be tolerant to rain, wind and to temperatures from about 5° C. to about 35° C.

It is claimed:

1. A new and distinct cultivar of *Euryops* plant named 'Straesun', as illustrated and described.

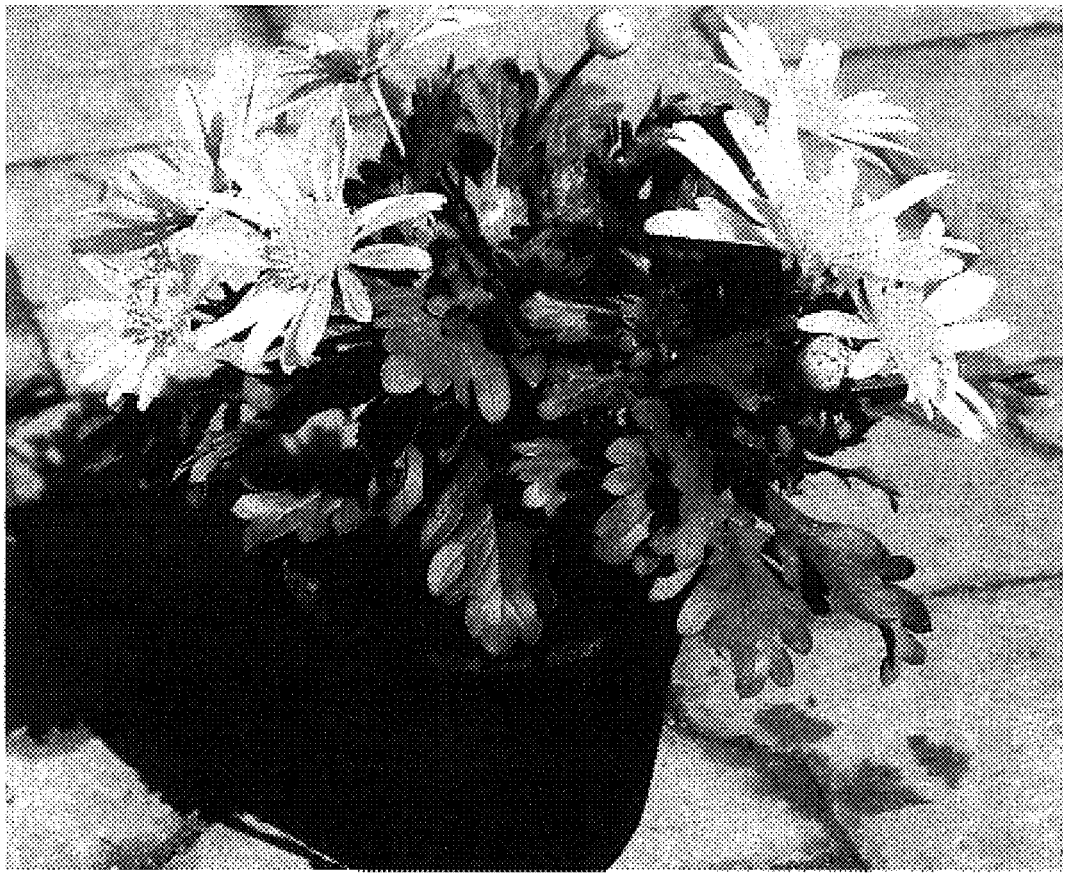

* * * * *